(12) United States Patent
Frommer et al.

(10) Patent No.: US 6,620,610 B2
(45) Date of Patent: Sep. 16, 2003

(54) **DNA SEQUENCE FROM *ARABIDOPSIS THALIANA* ENCODING AMMONIUM TRANSPORTER, AND PLASMIDS, BACTERIA AND YEAST COMPRISING THE DNA SEQUENCE**

(75) Inventors: Wolf-Bernd Frommer, Berlin (DE); Olaf Ninnemann, Berlin (DE)

(73) Assignee: Hoechst Scering AgrEvo GmbH, Berlin (DE)

( * ) Notice: Subject to any disclaimer, the term of this patent is extended or adjusted under 35 U.S.C. 154(b) by 0 days.

(21) Appl. No.: 08/635,967

(22) PCT Filed: Oct. 24, 1994

(86) PCT No.: PCT/EP94/03499

§ 371 (c)(1),
(2), (4) Date: Apr. 29, 1996

(87) PCT Pub. No.: WO95/11978

PCT Pub. Date: May 4, 1995

(65) Prior Publication Data

US 2001/0003848 A1 Jun. 14, 2001

(30) Foreign Application Priority Data

Oct. 28, 1993 (DE) .......................................... 43 37 597

(51) Int. Cl.[7] .............................. C12N 1/19; C12N 1/21; C12N 15/29; C12N 15/82
(52) U.S. Cl. ............................... 435/254.2; 435/252.3; 435/320.1; 536/23.6
(58) Field of Search ............................... 536/23.1, 24.5, 536/24.32; 435/320.1, 69.1, 252.3, 254.11, 240.4, 254.2; 800/200; 530/350; 436/94

(56) References Cited

PUBLICATIONS

Stitt et al., Regulation of metabolism in transgenic plants, Annu. Rev. Plant Physiol. Plant Mol. Biol., vol. 46, pp 341–68, 1995.*
Ninnemenn et al., Identification of a high affinity NH4+ transporter from plants, Embo, vol. 13(15), pp 3464–3471, Aug. 1, 1994.*
Stam M, et al., "The silence of genes in transgenic plants." Ann. Bot. 79: 3–12, 1997.*
Koziel MG, et al. "Optimizing expression of transgenes with an emphasis on post–transcriptional events." Plant Mol. Biol. 32 393–405, 1996.*
Smith CJS et al. "Antisense RNA inhibition of polygalacturonase gene expression in transgenic tomatoes." Nature 334: 724–726, Aug. 25, 1988.*
Fabiny JM, et al. Ammonium transport in *Escherichia coli*: Localization and nucleotide sequence of the amtA gene J. Gen. Microbiol. 137: 983–989, 1991.*
De Block M. "The cell biology of plant transformation: Current state, problems, prospects and the implications for the plant breeding." Euphytica 71: 1–14, 1993.*
Ninnemann O, et al. "Identification of a high affinity NH4 transporter from plants." EMBO J. 13: 3464–3471, 1994.*
Frank–Roman Lauter et al., Institut für Genbiologische Forschung, Ihnestrasse 63, Berlin, Germany; Preferential expression of an ammonium transporter and of two putative nitrate transporters in root hairs of tomato; Proc. Natl. Acad. Sci. U.S.A., vol. 93 pp. 8139–8144, Jul. 1996; Plant Biology.
Embo Journal, vol. 13, No. 15, Aug. 1, 1994, Eynsham, Oxford GB, pp. 3464–3471 Ninnemann, O., et al. 'Identification of a high affinity NH4+ transporter from plants' see the whole document.
Plant physiology, vol. 96, No. 1, May 1991 p. 145 Wang, M., et al. 'The mechanism of ammonium uptake by rice roots' see abstract 957.
J. Gen. Microbiol., vol. 137, No. 4, Apr. 1991 pp. 983–989 Fabiny, J. M. et al. 'Ammonium transport in *Escherichia coli*: localization and nucleotide sequence of the amtA gene ' see the whole document.
EMBL Sequence Database Release 33 Accession No. Z18087 Nov. 6, 1992 A. thaliana transcribed sequence.

* cited by examiner

Primary Examiner—Amy J. Nelson
(74) Attorney, Agent, or Firm—Frommer Lawrence & Haug LLP

(57) ABSTRACT

There are described DNA sequences from *Arabidopsis thaliana*, that contain the coding region of ammonium transporters. There are further described plasmids, bacteria, and yeast strains, which contain the sequences of ammonium transporters as a constituent of a recombinant DNA,

9 Claims, No Drawings

```
                         SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 1748 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
         (A) ORGANISM: Arabidopsis thaliana
         (C) INDIVIDUAL ISOLATE: Ammonium transporter (vii) IMMEDIATE SOURCE:
          (A) LIBRARY: cDNA library in plasmid pF161

(viii) POSITION IN GENOME:
           (B) MAP POSITION: from 21 to 1523 coding region (ix) FEATURE:
         (A) NAME/KEY: CDS
         (B) LOCATION: 21..1526

(xi) SEQUENCE DESCRIPTION: SEQ ID NO:1:

TTCTTCTCTA AACTCTCAAC ATG TCT TGC TCG GCC ACC GAT CTC GCC GTC           50
                     Met Ser Cys Ser Ala Thr Asp Leu Ala Val
                      1               5                  10

CTG TTG GGT CCT AAT GCC ACG GCG GCG GCC AAC TAC ATA TGT GGC CAG         98
Leu Leu Gly Pro Asn Ala Thr Ala Ala Ala Asn Tyr Ile Cys Gly Gln
                 15                  20                  25

CTA GGC GAC GTC AAC AAC AAA TTC ATC GAC ACC GCT TTC GCT ATA GAC        146
Leu Gly Asp Val Asn Asn Lys Phe Ile Asp Thr Ala Phe Ala Ile Asp
             30                  35                  40

AAC ACT TAC CTC CTC TTC TCC GCC TAC CTT GTC TTC TCT ATG CAG CTT        194
Asn Thr Tyr Leu Leu Phe Ser Ala Tyr Leu Val Phe Ser Met Gln Leu
             45                  50                  55

GGC TTC GCT ATG CTC TGT GCC GGT TCC GTG AGA GCC AAG AAT ACT ATG        242
Gly Phe Ala Met Leu Cys Ala Gly Ser Val Arg Ala Lys Asn Thr Met
     60                  65                  70

AAC ATC ATG CTT ACC AAC GTC CTT GAC GCT GCA GCC GGT GGT CTC TTC        290
Asn Ile Met Leu Thr Asn Val Leu Asp Ala Ala Ala Gly Gly Leu Phe
 75                  80                  85                  90
```

```
TAT TAT CTG TTT GGC TAC GCC TTT GCC TTT GGA TCT CCG TCC AAT GGT      338
Tyr Tyr Leu Phe Gly Tyr Ala Phe Ala Phe Gly Ser Pro Ser Asn Gly
            95                  100                 105

TTC ATC GGT AAA CAC TAC TTT GGT CTC AAA GAC ATC CCC ACG GCC TCT      386
Phe Ile Gly Lys His Tyr Phe Gly Leu Lys Asp Ile Pro Thr Ala Ser
            110                 115                 120

GCT GAC TAC TCC AAC TTT CTC TAC CAA TGG GCC TTT GCA ATC GCT GCG      434
Ala Asp Tyr Ser Asn Phe Leu Tyr Gln Trp Ala Phe Ala Ile Ala Ala
            125                 130                 135

GCT GGA ATC ACA AGT GGC TCG ATC GCT GAA CGG ACA CAG TTC GTG GCT      482
Ala Gly Ile Thr Ser Gly Ser Ile Ala Glu Arg Thr Gln Phe Val Ala
    140                 145                 150

TAC CTA ATC TAT TCC TCT TTC TTA ACC GGG TTT GTT TAC CCG GTC GTC      530
Tyr Leu Ile Tyr Ser Ser Phe Leu Thr Gly Phe Val Tyr Pro Val Val
155                 160                 165                 170

TCT CAC TGG TTC TGG TCA GTT GAT GGA TGG GCC AGC CCG TTC CGT ACC      578
Ser His Trp Phe Trp Ser Val Asp Gly Trp Ala Ser Pro Phe Arg Thr
            175                 180                 185

GAT GGA GAT TTG CTT TTC AGC ACC GGA GCG ATA GAT TTC GCT GGG TCC      626
Asp Gly Asp Leu Leu Phe Ser Thr Gly Ala Ile Asp Phe Ala Gly Ser
            190                 195                 200

GGT GTT GTT CAT ATG GTC GGA GGT ATC GCT GGA CTC TGG GGT GCG CTC      674
Gly Val Val His Met Val Gly Gly Ile Ala Gly Leu Trp Gly Ala Leu
            205                 210                 215

ATC GAA GGT CCA CGA CTT GGC CGG TTC GAT AAC GGA GGC CGT GCC ATC      722
Ile Glu Gly Pro Arg Leu Gly Arg Phe Asp Asn Gly Gly Arg Ala Ile
    220                 225                 230

GCT CTT CGT GGC CAC TCG GCG TCA CTT GTT GTC CTT GGA ACA TTC CTC      770
Ala Leu Arg Gly His Ser Ala Ser Leu Val Val Leu Gly Thr Phe Leu
235                 240                 245                 250

CTC TGG TTT GGA TGG TAC GGA TTT AAC CCC GGT TCC TTC AAC AAG ATC      818
Leu Trp Phe Gly Trp Tyr Gly Phe Asn Pro Gly Ser Phe Asn Lys Ile
            255                 260                 265

CTA GTC ACG TAC GAG ACA GGC ACA TAC AAC GGC CAG TGG AGC GCG GTC      866
Leu Val Thr Tyr Glu Thr Gly Thr Tyr Asn Gly Gln Trp Ser Ala Val
            270                 275                 280

GGA CGG ACA GCT GTC ACA ACA ACG TTA GCT GGC TGC ACC GCG GCG CTG      914
Gly Arg Thr Ala Val Thr Thr Thr Leu Ala Gly Cys Thr Ala Ala Leu
            285                 290                 295

ACA ACC CTA TTT GGG AAA CGT CTA CTC TCG GGA CAT TGG AAC GTC ACT      962
Thr Thr Leu Phe Gly Lys Arg Leu Leu Ser Gly His Trp Asn Val Thr
            300                 305                 310

GAT GTA TGC AAC GGC CTC CTC GGA GGG TTT GCA GCC ATA ACT GGT GGC     1010
Asp Val Cys Asn Gly Leu Leu Gly Gly Phe Ala Ala Ile Thr Gly Gly
315                 320                 325                 330

TGC TCT GTC GTT GAG CCA TGG GCT GCG ATC ATC TGC GGG TTC GTG GCG     1058
Cys Ser Val Val Glu Pro Trp Ala Ala Ile Ile Cys Gly Phe Val Ala
            335                 340                 345

GCC CTA GTC CTC CTC GGA TGC AAC AAG CTC GCT GAG AAG CTC AAA TAC     1106
Ala Leu Val Leu Leu Gly Cys Asn Lys Leu Ala Glu Lys Leu Lys Tyr
            350                 355                 360

GAC GAC CCT CTT GAG GCA GCA CAA CTA CAC GGT GGT TGC GGT GCG TGG     1154
Asp Asp Pro Leu Glu Ala Ala Gln Leu His Gly Gly Cys Gly Ala Trp
            365                 370                 375

GGA CTA ATA TTC ACG GCT CTC TTC GCT CAA GAA AAG TAC TTG AAC CAG     1202
Gly Leu Ile Phe Thr Ala Leu Phe Ala Gln Glu Lys Tyr Leu Asn Gln
            380                 385                 390

ATT TAC GGC AAC AAA CCC GGA AGG CCA CAC GGT TTG TTT ATG GGC GGT     1250
Ile Tyr Gly Asn Lys Pro Gly Arg Pro His Gly Leu Phe Met Gly Gly
```

-continued

```
                                                                                1298
GGA GGA AAA CTA CTT GGA GCT CAG CTG ATT CAG ATT GTG ATC ACG
Gly Gly Lys Leu Leu Gly Ala Gln Leu Ile Gln Ile Val Ile Thr
            415                 420                 425

1346
GGT TGG GTA AGT GCG ACC ATG GGG ACA CTT TTC TTC ATC CTC AAG AAA
Gly Trp Val Ser Ala Thr Met Gly Thr Leu Phe Phe Ile Leu Lys Lys
            430                 435                 440

1394
ATG AAA TTG TTG CGG ATA TCG TCC GAG GAT GAG ATG GCC GGT ATG GAT
Met Lys Leu Leu Arg Ile Ser Ser Glu Asp Glu Met Ala Gly Met Asp
            445                 450                 455

1442
ATG ACC AGG CAC GGT GGT TTT GCT TAT ATG TAC TTT GAT GAT GAT GAG
Met Thr Arg His Gly Gly Phe Ala Tyr Met Tyr Phe Asp Asp Asp Glu
            460                 465                 470

1490
TCT CAC AAA GCC ATT CAG CTT AGG AGA GTT GAG CCA CGA TCT CCT TCT
Ser His Lys Ala Ile Gln Leu Arg Arg Val Glu Pro Arg Ser Pro Ser
475                 480                 485                 490

1536
CCT TCT GGT GCT AAT ACT ACA CCT ACT CCG GTT TGA TTTGGATTTT
Pro Ser Gly Ala Asn Thr Thr Pro Thr Pro Val  *
            495                 500

TACTTTTATT CTCTATTTTC TAGAGTATTA TTTTAAATGA TGTTTTGTGA TACTTAAATA    1596

TTGTTTTGGA TATTTTTTTG GCATTTCAGT AATGTTTTAG ATGTACAGTT TCATGGGGTT    1656

GTGATGATAA TATCTATGTG GTCATTTGTG TTCTCTTTGG AGTTAAAAAA AAAAAAAAAA    1716

AAAAAAAAAA AAAAAAAAAA AAAAAAAAAA AA                                  1748
```

(2) INFORMATION FOR SEQ ID NO:2:

(i) SEQUENCE CHARACTERISTICS:
        (A) LENGTH: 501 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ser Cys Ser Ala Thr Asp Leu Ala Val Leu Leu Gly Pro Asn Ala
 1               5                  10                  15

Thr Ala Ala Asn Tyr Ile Cys Gly Gln Leu Gly Asp Val Asn Asn
            20                  25                  30

Lys Phe Ile Asp Thr Ala Phe Ala Ile Asp Asn Thr Tyr Leu Leu Phe
            35                  40                  45

Ser Ala Tyr Leu Val Phe Ser Met Gln Leu Gly Phe Ala Met Leu Cys
50                  55                  60

Ala Gly Ser Val Arg Ala Lys Asn Thr Met Asn Ile Met Leu Thr Asn
65                  70                  75                  80

Val Leu Asp Ala Ala Ala Gly Gly Leu Phe Tyr Tyr Leu Phe Gly Tyr
            85                  90                  95

Ala Phe Ala Phe Gly Ser Pro Ser Asn Gly Phe Ile Gly Lys His Tyr
            100                 105                 110

Phe Gly Leu Lys Asp Ile Pro Thr Ala Ser Ala Asp Tyr Ser Asn Phe
            115                 120                 125

Leu Tyr Gln Trp Ala Phe Ala Ile Ala Ala Gly Ile Thr Ser Gly
            130                 135                 140

Ser Ile Ala Glu Arg Thr Gln Phe Val Ala Tyr Leu Ile Tyr Ser Ser
145                 150                 155                 160

Phe Leu Thr Gly Phe Val Tyr Pro Val Val Ser His Trp Phe Trp Ser
            165                 170                 175
```

```
Val Asp Gly Trp Ala Ser Pro Phe Arg Thr Asp Gly Asp Leu Leu Phe
            180                 185                 190

Ser Thr Gly Ala Ile Asp Phe Ala Gly Ser Gly Val Val His Met Val
        195                 200                 205

Gly Gly Ile Ala Gly Leu Trp Gly Ala Leu Ile Glu Gly Pro Arg Leu
        210                 215                 220

Gly Arg Phe Asp Asn Gly Gly Arg Ala Ile Ala Leu Arg Gly His Ser
225                 230                 235                 240

Ala Ser Leu Val Val Leu Gly Thr Phe Leu Leu Trp Phe Gly Trp Tyr
                245                 250                 255

Gly Phe Asn Pro Gly Ser Phe Asn Lys Ile Leu Val Thr Tyr Glu Thr
                260                 265                 270

Gly Thr Tyr Asn Gly Gln Trp Ser Ala Val Gly Arg Thr Ala Val Thr
            275                 280                 285

Thr Thr Leu Ala Gly Cys Thr Ala Ala Leu Thr Thr Leu Phe Gly Lys
        290                 295                 300

Arg Leu Leu Ser Gly His Trp Asn Val Thr Asp Val Cys Asn Gly Leu
305                 310                 315                 320

Leu Gly Gly Phe Ala Ala Ile Thr Gly Gly Cys Ser Val Val Glu Pro
                325                 330                 335

Trp Ala Ala Ile Ile Cys Gly Phe Val Ala Ala Leu Val Leu Leu Gly
            340                 345                 350

Cys Asn Lys Leu Ala Glu Lys Leu Lys Tyr Asp Asp Pro Leu Glu Ala
            355                 360                 365

Ala Gln Leu His Gly Gly Cys Gly Ala Trp Gly Leu Ile Phe Thr Ala
        370                 375                 380

Leu Phe Ala Gln Glu Lys Tyr Leu Asn Gln Ile Tyr Gly Asn Lys Pro
385                 390                 395                 400

Gly Arg Pro His Gly Leu Phe Met Gly Gly Gly Lys Leu Leu Gly
                405                 410                 415

Ala Gln Leu Ile Gln Ile Ile Val Ile Thr Gly Trp Val Ser Ala Thr
            420                 425                 430

Met Gly Thr Leu Phe Phe Ile Leu Lys Lys Met Lys Leu Leu Arg Ile
        435                 440                 445

Ser Ser Glu Asp Glu Met Ala Gly Met Asp Met Thr Arg His Gly Gly
    450                 455                 460

Phe Ala Tyr Met Tyr Phe Asp Asp Glu Ser His Lys Ala Ile Gln
465                 470                 475                 480

Leu Arg Arg Val Glu Pro Arg Ser Pro Ser Pro Ser Gly Ala Asn Thr
                485                 490                 495

Thr Pro Thr Pro Val
            500
```

DNA SEQUENCE FROM *ARABIDOPSIS THALIANA* ENCODING AMMONIUM TRANSPORTER, AND PLASMIDS, BACTERIA AND YEAST COMPRISING THE DNA SEQUENCE

BACKGROUND OF THE INVENTION

The present invention relates to DNA sequences that contain the coding region of ammonium transporters, whose introduction into a plant genome modifies the uptake and transfer of nitrogen compounds in transgenic plants. As well as to plasmids, bacteria, yeasts, plant cells and plants containing these DNA sequences, and also to a process for the identification and isolation of DNA sequences that code for an ammonium transporter.

The supplying of growing plants with nitrogen compounds is a limiting factor in biomass production and is thus a limit on the yield of agricultural production. For this reason, nitrogen compounds, often in the form of mineral fertilisers, are added in agricultural biomass production.

An only partial uptake by the plants of the added nitrogen compounds makes it, on the one hand, necessary that the nitrogen fertiliser produced with high energy input is used in an excess, and, on the other hand, leads only to a partial uptake so that the nitrogen compounds are washed into the ground water which can lead to considerable ecological problems.

There is thus a great interest in plants which are capable of taking up large amounts of nitrogen as well as in the provision of the possibility of modifying the nitrogen uptake in plants.

For many plants there is provided information that the uptake of nitrogen is essentially in the form of nitrate salts. In strongly acid soils or in soils which follow intensive cultivation or have a strong tannin content, the nitrate formation (nitrification) is however strongly reduced and the uptake of nitrogen in the form of ammonium becomes the most important mechanism for the uptake of nitrogen compounds (Raven & Smith 1976 New Phytol 76: 415–431). Plants which are well adapted to acid soils, appear in part to favour ammonium rather than nitrate uptake and can tolerate ammonium ion concentrations that would be toxic for other plants. Examples of these plants are sugar cane, *Betula verucosa* or *Lolium rigidum* (Foy et al 1978, Ann Rev Plant Physiol 29: 511–566). The toxicity of the ammonium follows from a displacement of the ion balance: the uptake of the positively charged ammonium ion leads to an acidification of the cytoplasm, provided that no cations are secreted in counter-exchange. In an uptake of ammonium via a transport system whose uptake mechanism is based on an ammonium ion proton antiport, the ionic imbalance is not a problem.

There is thus a great interest in transport systems which work by the mechanism of an ammonium ion proton antiport and/or in systems which could be converted through techniques of protein engineering into ammonium ion proton antiports.

In spite of extensive efforts, it has not been possible up until now to isolate transport systems with whose help plants are protected against an ammonium ion loss caused by membrane diffusion (retrieval system).

By the term ammonium is also to be understood methylamine which is analogous to ammonium.

An active uptake system has been investigated in the fungus *Aspergillus nidulans* (e.g Arst et al., 1973, Mol Gen Genet 121: 239–245), as well as in *Penicillum chrysogenum* (Hackefte et al., J Biol Chem 245: 4241–4250). In these studies methylamine was used as the ammonium analogue. For *Aspergillus nidulans,* five genetic loci were established, which take part in the transport of methylamine (Pateman et al., 1973, J Bacteriol 114: 943–950). In biochemical experiments concerning the methylammonium transport in *Penicillum chrysogenum* and *Saccharomyces cerevisisae,* it has been shown that the transport is temperature and pH dependent, and that the pH optimum is 6.0 to 6.5 and the transport efficiency steadily rises up to a temperature of 35° C. (Roon et al., 1975, J Bacteriol 122: 502–509). The methylamine and/or ammonium transport in *Saccharomyces cerevisiae* is dependent on the supply of easily usable chemical energy, e.g. in form of glucose. The transport system consists of at least three independent transporters, which differ in transport capacity and affinity for the substrate: besides a high affinity transporter with low capacity (Km value=250 $\mu$M, maximum speed Vmax=20 nmol/min per mg cells (dry weight)) there is a low affinity system with high capacity (Km=2 mM, Vmax=50 nmol/min per mg cells) and a low affinity system with medium capacity (Km=20 mM, Vmax=33 nmol/min per mg cells) (Dubois & Grenson, 1979, Mol Gen Genet 175: 67–76). In the presence of glutamine or asparagine in the surrounding medium, the ammonium uptake is reduced by 60 to 70%, while other amines hardly have any influence (Roon et al., 1975, J Bacteriol 122: 502–509).

Nothing is known about the molecular nature of the ammonium transporter of the above-mentioned or different fungi and other organisms, such as for example bacteria. Equally nothing is known about systems, with whose help fungi or bacteria protect against ammonium ion loss by membrane diffusion (retrieval systems) at the molecular level. Further genes, which code for ammonium transporters are not known.

Various evidence suggests that the ammonium transport in *Saccharomyces cerevisiae* is accomplished by at least two functionally different transport systems (Dubois & Grenson, 1979, Mol Gen Genet 175: 67–76):

1. Kinetic analyses of the methylamine-uptake by Saccharomyces show an abrupt transition between apparent linear sections, whereby both functions are inhibitable by ammonium.
2. Both functions can be separately excluded by mutation. The resulting mutations mep-1 and mep-2 are genetically independent.
3. The mutants mep-1 and mep-2 can each grow in media with ammonium as the only nitrogen source, while a double mutant mep-1/mep-2 shows hardly any growth under these conditions (data taken from Dubois & Grenson, 1979).

A clarification of the ammonium transport processes in plants, that leads to similar detailed information such as for yeast, is not available and because of the difficulty of the molecular biological analysis of mutations is scarcely possible in a corresponding manner.

SUMMARY OF THE INVENTION

The object of the present invention is to provide coding for DNA-sequences of ammonium transporters which cause a change in the uptake and transfer of nitrogen compounds in transgenic plants.

The object of the present invention is further to provide DNA-constructs, such as plasmids, with which the ammonium transport in transgenic plants can be modified by introduction of the corresponding construct (plasmids) into the plant genome which leads upon transcription to the formation of a new ammonium transporter molecule in the transgenic plant and/or the suppression of the formation the plant's own ammonium transporter molecules.

There have now surprisingly been found DNA sequences, that contain the coding region of a plant ammonium transporter, whereby the information contained in the nucleotide sequence when integrated in a plant genome a) under the control of a promoter in a sense orientation makes the expression of a translatable mRNA which leads to the synthesis of an ammonium transporter in transgenic plants possible or b) under the control of a promoter in an anti-sense orientation makes the expression of a non-translatable mRNA which prevents the synthesis of an endogenous ammonium transporter in transgenic plants possible.

A further aspect of the invention is to provide DNA sequences which contain the coding region of a plant ammonium transporter.

In an analogous way, the ammonium transporter can also be used to modify animal cells.

The DNA sequences, which code for a plant ammonium transporter, can be identified and isolated by a process of determining which DNA sequences are able to complement specific mutations in the yeast *Saccharomyces cerevisiae*. In general, the mutations, are those which have the result that the corresponding strains cannot grow any further in media which contain ammonium as the only nitrogen source. Such a strain can be transformed with a plant cDNA-library and transformands can be selected which can grow in media which contain ammonium as the only nitrogen source.

A further aspect of the invention is a process for the identification and isolation of DNA sequences that code for ammonium transporters from plants, which includes the following steps:

a) transformation of a yeast strain which cannot grow in media which contains ammonium as the only nitrogen source with a plant cDNA-library using suitable expression vectors, b) selection and propagation of transformants, which after expression of plant cDNA-sequences, can grow in media which contain ammonium as the only nitrogen source, and c) isolation of the expression vectors which carry a plant cDNA insert from the selected transformand.

The yeast strain in process step a) is preferably one which cannot take up ammonium from the medium because of mutations in the transport systems for the ammonium uptake. Preferred is the double mutant mep1/mep2 (strain 26972c), described by Dubois & Grenson (1979, Mol. Gen. Genet. 175:67–76), and with which two uptake systems for ammonium are interrupted following mutation.

A further aspect of the invention is to provide DNA sequences from plants which are obtainable using the above described process and which code for a protein with the biological activity of an ammonium transporter.

Whether it is possible using such complementation process to identify DNA sequences which code for plant ammonium transporters depends on various factors. First the expression plasmid suitable for use in yeast must contain cDNA fragments which code for the plant ammonium transporter, that means the mRNA fundamental for the cDNA synthesis must result from tissues which express the ammonium transporter. Since nothing is known about plant ammonium transporters, tissues which code for the ammonium transporter are therefore also not know.

A further prerequisite for the success of the complementation strategy is that ammonium transport systems existing in plants can be functionally expressed in yeast, since only in this case is a complementation of the deficiency liberated by the mutation possible. Since nothing is known about plant ammonium transporters, it is also not known whether a functional expression in yeast is possible.

It has now further been surprisingly found that by expression of a cDNA library, for example from leaf tissue of *Arabidopsis thaliana*, by means of expression plasmids suitable for use in yeast which contain the promoter of phosphoglycerate kinase from yeast, the complementation of the double mutation mep-1/mep-2 is possible, if the expression plasmids contain specified plant cDNA fragments. These cDNA fragments code for plant ammonium transporters.

The identification of plant ammonium transporters is described here using *Arabidopsis thaliana* as an example, but it is not however limited to this plant species.

A cDNA fragment that codes for a plant ammonium transporter containing for example the following sequence. (Seq. ID No.1):

```
                                            TTCTTCTCTAAACTCTCAAC    20

ATG TCT TGG TCG GCC ACC GAT CTC GCC GTC CTG TTG GGT CCT AAT    65
Met Ser Cys Ser Ala Thr Asp Leu Ala Val Leu Leu Gly Pro Asn

GCC ACG GCG GCG GCC AAC TAC ATA TGT GGC CAG CTA GGC GAC GTC    110
Ala Thr Ala Ala Ala Asn Tyr Ile Cys Gly Gln Leu Gly Asp Val

AAC AAC AAA TTC ATC GAC ACC GCT TTC GCT ATA GAC AAC ACT TAC    155
Asn Asn Lys Phe Ile Asp Thr Ala Phe Ala Ile Asp Asn Thr Tyr

CTC CTC TTC TCC GCC TAC CTT GTC TTC TCT ATG CAG CTT GGC TTC    200
Leu Leu Phe Ser Ala Tyr Leu Val Phe Ser Met Gln Leu Gly Phe
```

```
GCT ATG CTC TGT GCC GGT TCC GTG AGA GCC AAG AAT ACT ATG AAC   245
Ala Met Leu Cys Ala Gly Ser Val Arg Ala Lys Asn Thr Met Asn

ATC ATG CTT ACC AAC GTC CTT GAC GCT GCA GCC GGT GCT CTC TTC   290
Ile Met Leu Thr Asn Val Leu Asp Ala Ala Ala Gly Ala Leu Phe

TAT TAT CTG TTT GGC TAC GCC TTT GCC TTT GGA TCT CCG TCC AAT   335
Tyr Tyr Leu Phe Gly Tyr Ala Phe Ala Phe Gly Ser Pro Ser Asn

GGT TTC ATC GGT AAA CAC TAC TTT GGT CTC AAA GAC ATC CCC ACG   380
Gly Phe Ile Gly Lys His Tyr Phe Gly Leu Lys Asp Ile Pro Thr

GCC TCT GCT GAC TAC TCC AAC TTT CTC TAC CAA TGG GCC TTT GCA   425
Ala Ser Ala Asp Tyr Ser Asn Phe Leu Tyr Gln Trp Ala Phe Ala

ATC GCT GCG GCT GGA ATC ACA AGT GGC TCG ATC GCT GAA CGG ACA   470
Ile Ala Ala Ala Gly Ile Thr Ser Gly Ser Ile Ala Glu Arg Thr

CAG TTC GTG GCT TAC CTA ATC TAT TCC TCT TTC TTA ACC GGG TTT   515
Gln Phe Val Ala Tyr Leu Ile Tyr Ser Ser Phe Leu Thr Gly Phe

GTT TAC CCG GTC GTC TCT CAC TGG TTC TGG TCA GTT GAT GGA TGG   560
Val Tyr Pro Val Val Ser His Trp Phe Trp Ser Val Asp Gly Trp

GCC AGC CCG TTC CGT ACC GAT GGA GAT TTG CTT TTC AGC ACC GGA   605
Ala Ser Pro Phe Arg Thr Asp Gly Asp Leu Leu Phe Ser Thr Gly

GCG ATA GAT TTC GCT GGG TCC GGT GTT GTT CAT ATG GTC GGA GGT   650
Ala Ile Asp Phe Ala Gly Ser Gly Val Val His Met Val Gly Gly

ATC GCT GGA CTC TGG GGT GCG CTC ATC GAA GGT CCA CGA CTT GGC   695
Ile Ala Gly Leu Trp Gly Ala Leu Ile Glu Gly Pro Arg Leu Gly

CGG TTC GAT AAC GGA GGC CGT GCC ATC GCT CTT CGT GGC CAC TCG   740
Arg Phe Asp Asn Gly Gly Arg Ala Ile Ala Leu Arg Gly His Ser

GCG TCA CTT GTT GTC CTT GGA ACA TTC CTC CTC TGG TTT GGA TGG   785
Ala Ser Leu Val Val Leu Gly Thr Phe Leu Leu Trp Phe Gly Trp

TAC GGA TTT AAC CCC GGT TCC TTC AAC AAG ATC CTA GTC ACG TAC   830
Tyr Gly Phe Asn Pro Gly Ser Phe Asn Lys Ile Leu Val Thr Tyr

GAG ACA GGC ACA TAC AAC GGC CAG TGG AGC GCG GTC GGA CGG ACA   875
Glu Thr Gly Thr Tyr Asn Gly Gln Trp Ser Ala Val Gly Arg Thr

GCT GTC ACA ACA ACG TTA GCT GGC TGC ACC GCG GCG CTG ACA ACC   920
Ala Val Thr Thr Thr Leu Ala Gly Cys Thr Ala Ala Leu Thr Thr

CTA TTT GGG AAA CGT CTA CTC TCG GGA CAT TGG AAC GTC ACT GAT   965
Leu Phe Gly Lys Arg Leu Leu Ser Gly His Trp Asn Val Thr Asp

GTA TGC AAC GGC CTC CTC GGA GGG TTT GCA GCC ATA ACT GGT GGC  1010
Val Cys Asn Gly Leu Leu Gly Gly Phe Ala Ala Ile Thr Gly Gly

TGC TCT GTC GTT GAG CCA TGG GCT GCG ATC ATC TGC GGG TTC GTG  1055
Cys Ser Val Val Glu Pro Trp Ala Ala Ile Ile Cys Gly Phe Val

GCG GCC CTA GTC CTC CTC GGA TGC AAC AAG CTC GCT GAG AAG CTC  1100
Ala Ala Leu Val Leu Leu Gly Cys Asn Lys Leu Ala Glu Lys Leu

AAA TAC GAC GAC CCT CTT GAG GCA GCA CAA CTA CAC GGT GGT TGC  1145
Lys Tyr Asp Asp Pro Leu Glu Ala Ala Gln Leu His Gly Gly Cys

GGT GCG TGG GGA CTA ATA TTC ACG GCT CTC TTC GCT CAA GAA AAG  1190
Gly Ala Trp Gly Leu Ile Phe Thr Ala Leu Phe Ala Gln Glu Lys

TAC TTG AAC CAG ATT TAC GGC AAC AAA CCC GGA AGG CCA CAC CGT  1235
Tyr Leu Asn Gln Ile Tyr Gly Asn Lys Pro Gly Arg Pro His Arg

TTG TTT ATG GGC GGT GGA GGA AAA CTA CTT GGA GCT CAG CTG ATT  1280
Leu Phe Met Gly Gly Gly Gly Lys Leu Leu Gly Ala Gln Leu Ile

CAG ATC ATT GTG ATC ACG GGT TGG GTA AGT GCG ACC ATG GGG ACA  1325
Gln Ile Ile Val Ile Thr Gly Trp Val Ser Ala Thr Met Gly Thr

CTT TTC TTC ATC CTC AAG AAA ATG AAA TTG TTG CGG ATA TCG TCC  1370
Leu Phe Phe Ile Leu Lys Lys Met Lys Leu Leu Arg Ile Ser Ser

GAG GAT GAG ATG GCC GGT ATG GAT ATG ACC AGG CAC GGT GGT TTT  1415
```

```
                         -continued
Glu Asp Glu Met Ala Gly Met Asp Met Thr Arg His Gly Gly Phe GCT TAT ATG TAC TTT GAT GAT GAT GAG TCT CAC AAA GCC ATT CAG  1460
Ala Tyr Met Tyr Phe Asp Asp Asp Glu Ser His Lys Ala Ile Gln CTT AGG AGA GTT GAG CCA CGA TCT CCT TCT CCT TCT GGT GCT AAT  1505
Leu Arg Arg Val Glu Pro Arg Ser Pro Ser Pro Ser Gly Ala Asn ACT ACA CCT ACT CCG GTT TGATTTGGAT TTTTACTTTT ATTCTCTATT     1553
Thr Thr Pro Thr Pro Val

TTCTAGAGTA TTATTTTAAA TGATGTTTTG TGATACTTAA ATATTGTTTT        1603

GGATATTTTT TTGGCATTTC AGTAATGTTT TAGATGTACA GTTTCATGGG        1653

GTTGTGATGA TAATATCTAT GTGGTCATTT GTGTTCTCTT TGGAGTTAAA        1703

AAAAAAAAAA AAAAAAAAAA AAAAAAAAAA AAAAAAAAA AAAA              1748
```

The DNA sequences of the invention, identified using the transformed yeast strain, such as e.g. the sequence Seq. ID No. 1, can be introduced into plasmids and thereby be combined with regulatory elements for expression in eukaryotic cells (see Example 4). These regulatory elements are, on the one hand, transcription promoters, and, on the other hand, transcription terminators. With the plasmids, eukaryotic cells can be transformed, with the aim of expression of a translatable mRNA which makes possible the synthesis of an ammonium transporter in the cells (sense orientation) or with the aim of expression of a non-translatable RNA which prevents the synthesis of an endogenous ammonium transporter in the cells (anti-sense orientation).

These plasmids are also an aspect of the invention.

Preferred plasmids are plasmids p35S-MEP-a and p35S-a-MEP-a, which have been deposited at the Deutsche Sammlung von Mikroorganismen (DSM).

A still further aspect of the present invention are yeasts which contain the DNA sequences of the invention.

The yeast strains used for the identification of a plant methylamine or ammonium transporter can be used to study the properties of the transporter as well as its substrate. The DNA sequences of a plant ammonium transporter present in plasmids can, in accordance with results of these studies, be subjected to a mutagenesis or sequence modification by recombination in order to change the properties of the transporter. By changing the specificity of the transport system, the transport of new compounds is possible, which opens up interesting applications (see below). In addition, by suitable change of the transporter, the transport mechanism can be modified. One can envisage, especially but not exclusively, a change, that modifies the cotransport properties of the transporter, for example with the effect that this results in an ammonium ion-proton-antiport, which prevents a toxicity of ammonium ions taken up for plants as a result of acidification of the cytoplasm. In this way, the yeast strain of the invention, which contains the cDNA sequence of a plant ammonium transporter in an expression plasmid, can be used for a mutation selection system.

By expression of an RNA, corresponding to the DNA sequences of the invention, of plant ammonium transporters in transgenic plants it is possible to have a change of the plant nitrogen metabolism, whose economic significance is obvious. Nitrogen is the nutrient mainly responsible for limiting growth. The viability of seedlings as well as germination capacity of seeds is directly dependent on the nitrogen content of storage tissue. The formation of high value food materials with a high protein content is dependent on a sufficient nitrogen supply.

The change of nitrogen uptake, for example by addition of a new uptake system of nitrogen compounds such as ammonium, can thus lead to an increase in yield of transgenic crops, especially under nitrogen limitation. In this way, transgenic plants can be cultivated in high yields under low input conditions.

The possibility of suppressing the uptake of ammonium in the transgenic plants can however also be desirable under certain conditions. For example, one can envision the cultivation of transgenic plants on acid soils which are not suitable for growth. As a result of suppressing nitrification, ammonium ion concentrations on such soils could be present which would be toxic for certain plants. This is because the ammonium taken by the plants in the cells can no longer be fully metabolised and acts as a cell poison. The suppression of the uptake of ammonium by suppressing the biosynthesis of the ammonium transporter can thus alter transgenic plants to the extent that cultivation on acid soils becomes possible.

A further aspect of the present invention are transgenic plants in which the DNA sequences of the invention are introduced as a constituent of a recombinant DNA molecule, in which this recombinant DNA molecule is stably integrated into the genome, and in whose cells based on the presence of these sequences there is achieved either a synthesis of an additional plant ammonium transporter whereby these cells can take up larger amounts of ammonium in comparison with untransformed plants or there is achieved an inhibition of the synthesis of endogenous ammonium transporters whereby such cells show a reduced uptake of ammonium in comparison with untransformed cells.

Transgenic crops are, for example tobacco, potatoes, sugar beet, soya beans, peas, beans or maize.

The genetic modification of dicotyledonous and monocotyledonous plants can be carried out by currently known processes, (see for example Gasser, C. S., Fraley, R. T., 1989, Science 244:1293–1299; Potrykus, 1991, Ann Rev Plant Mol Biol Plant Physiol 42: 205–225). For expression in plants the coding sequences must be coupled with the transcriptional regulatory elements. Such elements called promoters, are known (see for example EP 375091).

Further, the coding regions must be provided with transcription termination signals with which they can be correctly transcribed. Such elements are also described (see Gielen et al., 1989, EMBO J 8: 23–29). The transcriptional start region can be both native and/or homologous as well as foreign and/or heterologous to the host plant. If desired, termination regions are interchangeable with one another. The DNA sequence of the transcription starting and termination regions can be prepared synthetically or obtained naturally, or obtained from a mixture of synthetic and natural DNA constituents. For the introduction of foreign genes into higher plants, a large number of cloning vectors are available that include a replication signal for E. coli and a marker which allows a selection of the transformed cells. Examples of such vectors are pBR 322, pUC-Series, M13 mp-Series, pACYC 184 etc. Depending on the method of introduction of the desired gene into the plants, other DNA sequences may be suitable. Should the Ti- or Ri-plasmid be used, e.g. for the transformation of the plant cell, then at least the right boundary, and often both the right and left boundary of the Ti- and Ri-Plasmid T-DNA, is attached as a flanking region to the gene being introduced. The use of T-DNA for the transformation of plants cells has been intensively researched and is well described in EP 120 516; Hoekama, In: The Binary Plant Vector System, Offsetdrukkerij Kanters B. V. Alblasserdam, (1985), Chapter V; Fraley, et al., Crit. Rev. Plant Sci., 4:1–46 and An et al. (1985) EMBO J. 4: 277–287. Once the introduced DNA is integrated in the genome, it is generally stable there and remains also in the offspring of the original transformed cells. It normally contains a selection marker, which induces resistance in the transformed plant cells against a biocide or antibiotic such as kanamycin, G 418, bleomycin, hygromycin or phosphinotricin etc. The individual marker employed should therefore allow the selection of transformed cells from cells which lack the introduced DNA.

For the introduction of DNA into a plant host cell, besides transformation using Agrobacteria, there are many other techniques available. These techniques include the fusion of protoplasts, microinjection of DNA and electroporation, as well as ballistic methods and virus infection. From the transformed plant material, whole plants can be regenerated in a suitable medium, which contains antibiotics or biocides for selection. The resulting plants can then be tested for the presence of introduced DNA.

A further aspect of the present invention is to provide transformed plant cells in which the DNA sequences of the invention are introduced as a constituent of a recombinant DNA molecule in which the recombinant DNA molecule is stably integrated into the genome. In the cells, based on the presence of these sequences, there is achieved either a synthesis of an additional plant ammonium transporter whereby the cells can take up larger amounts of ammonium in comparison with untransformed plants or there is achieved an inhibition of the synthesis of endogenous ammonium transporters whereby such cells show a reduced uptake of ammonium in comparison with untransformed cells.

No special demands are placed on the plasmids in injection and electroporation. Simple plasmids, such as e.g. pUC-derivatives can be used. Should however whole plants be regenerated from such transformed cells the presence of a selectable marker gene is necessary. The transformed cells grow within the plants in the usual manner (see also McCormick et al. (1986) Plant Cell Reports 5: 81–84). These plants can be grown normally and crossed with plants, that possess the same transformed genes or different genes. The resulting hybrid individuals have the corresponding phenotypical properties.

The introduction of DNA plant ammonium transporters for changing the uptake of nitrogen compounds is described here using Arabidopsis thaliana and tobacco as examples. The use is not however limited to this plant species. The DNA sequences of the invention can also be introduced in plasmids and thereby combined with steering elements for an expression in prokaryotic cells. The formation of a translatable RNA sequence of a eukaryotic ammonium transporter from bacteria leads, in spite of the considerable differences in the membrane structures of prokaryotes and eukaryotes, to the expression in prokaryotes of a functional eukaryotic ammonium transporter with its substrate specificity. This makes possible the production of bacterial strains which, as for the yeast strain used for identifying the ammonium transporter, could be used for studies of the properties of the transporter as well as its substrate, which opens up interesting applications.

The invention also relates to bacteria that contain the plasmids of the invention.

The DNA sequences of the invention can also be introduced in plasmids which allow mutagenesis or a sequence modification through recombination of DNA sequences using standard microbiological processes. In this way the specificity of the ammonium transporter can be modified.

Modified ammonium transporters can be used for example for the transformation of agriculturally useful transgenic plants, whereby both transport of pesticides and plant growth regulators to plants can be envisaged.

By using standard processes (see Sambrook et al., 1989, Molecular Cloning: A Laboratory Manual, 2. Edn., Cold Spring Harbor Laboratory Press, N.Y., USA), base exchanges can be carried out or natural or synthetic sequences can be added. In order to fuse DNA fragments with one another, adaptors or linkers can be added to the fragments. Further, manipulations can be carried out which prepare suitable restriction cleavage sides or to remove the excess DNA or restriction cleavage sites. Where insertions, deletions or substitutions such as, for example, transitions and transversions are to be carried out, in vitro mutagenesis, primer repair, restrictions or ligations can be used. For methods of analysis, in general, a sequence analysis, restriction analysis and other biochemical molecular biological methods can be used. After each manipulation the DNA sequence used, can be cleaved and fused with another DNA sequence. Each plasmid sequence can be cloned in the same or different plasmids.

The invention also relates to derivatives or parts of plasmids on which the DNA sequences of the invention are localised.

Derivatives or parts of the DNA sequences and plasmids of the invention can also be used for the transformation of prokaryotic and eukaryotic cells.

Further, the DNA sequences of the invention can be used according to standard processes for the isolation of homologous sequences from the genome of plants of various species, which also code for ammonium transporter molecules. With these sequences, constructs for the transformation of plant cells can be prepared which modify the transport processes in transgenic plants.

By the terms "homology" or "homologous sequences" are to be understood, a sequence identity of 60% to 80%, preferably 80% to 95% and especially 95% to 100%.

In order to specify related DNA sequences, gene libraries must first be prepared which are representative of the content of genes of a plant species or of the expression of genes in a plant species. The former are genomic libraries, while the latter are cDNA libraries. From these, related sequences can be isolated using the DNA sequences of the invention as probes. Once the related gene has been identified and isolated, a determination of the sequence and an analysis of the properties of the proteins coded from this sequence is possible.

DNA sequences of ammonium transporters obtained in this way are also part of the invention and could be used as described above.

The use of the DNA sequences as described above is also part of the invention.

A further aspect of the invention are DNA sequences from plants, which hybridise with DNA sequences of the invention and code for a protein that possesses the biological activity of an ammonium transporter. The term "hybridisation" means in this connection, a hybridisation under conventional hybridisation conditions, preferably under stringent conditions, such as described for example by Sambrook et al. (1989, Molecular Cloning, A Laboratory Manual, 2. Edn. Cold Spring Harbor Laboratory Press, Cold Spring Harbour, N.Y.). An important biological activity of an ammonium transporter is the capability of transporting ammonium or analogues thereof through biological membranes. This activity can be measured by uptake of ammonium or analogues thereof by cells which express the particular ammonium transporter, as described for example in example 3 of the present invention.

Deposits

The following plasmids were deposited at the Deutschen Sammlung von Mikroorganismen (DSM) in Braunschweig, Germany on the 26.10.1993 (deposit number):

| Plasmid | p35S-MEP-a | (DSM 8651) |
| Plasmid | p35S-a-MEP-a | (DSM 8652) |

BRIEF DESCRIPTION OF THE DRAWINGS

FIG. 1 shows the plasmid p35S-MEP-a which is a derivative of the plasmid pBIN19 (Bevan, M., 1984, Nucl Acids Res 12: 8711–8721). It comprises:

A=Fragment from the genome of the cauliflower mosaic virus that carries the 35S promoter (nt 6909–7437). The promoter fragment was prepared as an EcoRI/KpnI fragment from plasmid pDH51 (Pietrzak et al., Nucl. Acid Res. 14, 5857–5868).

B=NotI/NotI fragment of the cDNA with the coding region of the ammonium transporter of *Arabidopsis thaliana* in sense orientation to the fragment A. The arrow marked in fragment B indicates the reading direction of the cDNA.

C=Polyadenylation signal of the gene 3 of the T-DNA of the plasmid pTiACH5 (Gielen et al., EMBO J 3: 835–846), nucleotides 11749 to 11939, which was isolated as a PvuII/HindIII fragment from plasmid pAGV40 (Herrera-Estrella et al., Nature 303, 209–213) and, after the addition of SphI linker onto the PvuII cleavage site, was cloned between the SphI and HindIII cleavage sites of the polylinker from pBIN19.

FIG. 2 shows the plasmid p35S-a-MEP-a which is a derivative of the plasmid pBIN19 (Bevan, M., 1984, Nucl Acids Res 12: 8711–8721). It comprises:

A=Fragment from the genome of the cauliflower mosaic virus that carries the 35S promoter (nt 6909–7437). The promoter fragment was prepared as an EcoRI/KpnI fragment from plasmid pDH51 (Pietrzak et al., Nucl. Acid Res. 14, 5857–5868).

B=NotI/NotI fragment of the cDNA with the coding region of the ammonium transporter of *Arabidopsis thaliana* in anti-sense orientation to the fragment A. The arrow marked in fragment B indicates the reading direction of the cDNA.

C=Polyadenylation signal of the gene 3 of the T-DNA of the plasmid pTiACH5 (Gielen et al., EMBO J 3: 835–846), nucleotides 11749 to 11939, which was isolated as a PvuII/HindIII fragment from plasmid pAGV40 (Herrera-Estrella et al., Nature 303, 209–213) and, after the addition of SphI linker onto the PvuII cleavage site, was cloned between the SphI and HindIII cleavage sites of the polylinker from pBIN19.

DESCRIPTION OF THE PREFERRED EMBODIMENTS OF THE INVENTION

The following examples illustrate the invention without limiting it. The examples describe the cloning and identification as well as the function of a plant ammonium transporter and its use for the genetic modification of plants with the aim of changing the uptake and transfer of nitrogen compounds. In an analogous manner to the Examples, other plants especially crop plants such as potato, sugar beet, maize, etc, can be modified.

In Examples 1 to 4 the following standard processes and special techniques were used.

1. Cloning Process

For cloning in *E. coli*, a derivative of the vector pACYC that contains the polylinker from pBluescriptSK was used.

For the transformation of yeasts, the vector pFL61 (Minet & Lacroute, 1990,Curr Genet 18: 287–291) was used.

For the plant transformation the gene constructs were cloned in the binary vector pBinAR, a derivative of pBIN19 (Bevan, 1984, Nucl Acids Res 12: 8711–8721), was cloned (see Example 4).

2. Bacterial and Yeast Strains

For the pACYC vector as well as for pBinAR constructs, *E. coli* strain DH5α was used.

As starting strain for the production of the cDNA library in yeast, the yeast strain 26972c (Dubois & Grenson, 1979, Mol Gen Gnete 175: 67–76) with the mutations mep-1/mep-2 and ura3 was used.

The transformation of the plasmid in potato plants was carried out using *Agrobacterium tumefaciens* strain LBA4404 (Bevan (1984) Nucl. Acids Res 12: 8711–8720).

3. Transformation of *Agrobacterium tumefaciens*

The transfer of the DNA in the Agrobacteria was carried out by direct transformation by the method of Höfgen & Willmitzer (1988, Nucleic Acids Res 16: 9877). The plasmid DNA of the transformed Agrobacterium was isolated in accordance with the method of Birnboim and Doly (1979) (Nucl Acids Res 7: 1513–1523) and was analysed by gel electrophoresis after suitable restriction cleavage.

4. Plant Transformation

Tobacco 10 ml of an *Agrobacterium tumefaciens* overnight culture grown under selection was sedimented and resuspended in the same volume of antibiotic free medium. In a sterile petri dish, leaf discs of sterile plants (approximately 1 cm$^2$), the central vein of which had been removed, were immersed in this bacterial suspension. The leaf discs were then placed in a closely packed arrangement in petri dishes containing MS medium (Murashige et al. (1962) Physiologia Plantarum 15, 473–497) with 2% sucrose and 0.8% bacto agar. After two days of incubation in the dark at 25° C., the leaf discs were transferred onto MS medium containing 500 mg/l Claforan, 50 mg/l kanamycin, 1 mg/l benzylaminopurine (BAP), 0.2 mg/l of naphthylacetic acid (NAA) and 0.8% bacto agar. Growing shoots were transferred onto hormone-free MS medium with 250 mg/l Claforan and 50 mg/l Kanamycin.

*Arabidopsis thaliana*

Cotyledons from a seven day old sterile culture of *Arabidopsis thaliana* grown from seeds, were pre-incubated on Cl-Medium for two days with a layer of tobacco suspension culture (as feeder layer) and then for 5 minutes in a suspension with *Agrobacterium tumefaciens* (preparation of suspension see under tobacco transformation) and then incubated for two days on Cl-Medium with feeder layer in low light conditions. After this cocultivation with Agrobacteria the explantates were laid out on SIM I—medium, that was renewed weekly. After callous-formation, the explantates were set transplanted to SIM II—medium and then were cultivated under selection with kanamycin. Small shoots were separated from the callous material and transplanted to RI—Medium. After separation of seeds, these could be analysed.

The individual media were as follows:

| Cl-medium | SIM I - medium | SIM II - medium | RI-Medium |
|---|---|---|---|
| Murashige-Skoog medium with 2% sucrose, 8 g/l agar, 1 mg/l 2,4-dichlorophenoxy-acetic acid (2,4-D), 0.2 mg/l kinetin | Murashige-Skoog medium with 2% sucrose, 8 g/l agar, 1 mg/l 6-benzyl-aminopurine, 0.4 mg/l naphthyl-acetic acid, 0.5 g/l Claforan, 100 mg/l kanamycin | Murashige-Skoog medium with 2% sucrose, 8 g/l agar, 7 mg/l N$^6$-[2-iso-pentenyl]-adenine, 0.05 mg/l indolyl-acetic acid, 0.5 mg/l Claforan, 100 mg/l kanamycin | Murashige-Skoog medium with 1% sucrose, 8 g/l agar, 1 mg/l indolyl-butyric acid |

EXAMPLE 1

Cloning of the cDNA of a Plant Methylamine or Ammonium Transporter

For complementation of the ammonium transport double mutation of the yeast strain 26972c (Dubois & Grenson, 1979, Mol Gen Genet 175: 67–76), a cDNA of young germ lines from *Arabidopsis thaliana* (two leaf stage) was used in the yeast expression vector pFL61 (Minet & Lacroute, 1990, Curr Genet 18: 287–291) which had been made available by Minet (Minet et al., 1992, Plant J 2: 417–422). Around 1 μg of the vector with the cDNA-insert was transformed in the yeast strain 26972c by the method of Dohmen et al. (1991, Yeast 7: 691–692). Yeast transformands, which could grow in minimal medium with 1 mM NH$_4$Cl as the sole nitrogen source, were propagated. From the lines, plasmid-DNA was prepared by standard methods. This DNA was immediately transformed in strain 26972c. In this way, a plasmid, pFL61-MEP-a, was obtained that can complement the mep-1/mep-2 double mutation. This plasmid has an insertion of size 1.75 kbp.

The yeast strain 26972c::pFL61-MEP-a which was obtained by transformation of 26972c with plasmid pFL61-MEP-a can be used for uptake studies with methylamine or ammonium (see example 3). By genetic modification of the coding region of the ammonium transporter gene MEP-a by standard methods (cf. Sambrook et al., 1989, Molecular cloning: A laboratory manual, 2. Edn., Cold Spring Harbor Laboratory Press, NY, USA) the specificity or characteristic of the transport mechanism can be modified. The strain 26972c::pFL61-MEP-a is suitable for direct testing for inhibitors or promoters of the ammonium transport, using the ammonium transport system of the invention (see Example 3). The cDNA insertion of the plasmids pFL61-MEP-a can be used for the identification of similar DNA sequences from plants of other species or from other organisms, such as bacteria or animal systems. For this hybridisation techniques are usable. Likewise using the cDNA sequence, a construct for the expression of the gene product as a fusion protein in bacteria can be prepared by standard processes. Using the fusion protein, an antibody, which identifies similar proteins in other organisms, can be prepared.

EXAMPLE 2

Sequence Analyses of the cDNA Insert of the Plasmid pFL61-MEP-a

From a yeast line 26972c::pFL61-MEP-a, obtained from example 1, the plasmid pFL61-MEP-a was isolated and its cDNA insert prepared as a NotI fragment. The fragment was cloned in a modified pACYC vector (Chang & Cohen, 1978, J Bacteriol 134. 1141–1156), which contained, between a HincIII (nt 3211) and a filled HindIII (nt 1523) cutting position, the polylinker from pBluescript as BssHII fragment. Through the modification, the tetracycline resistance is lost. The cDNA fragment was cloned in the thus obtained vector pACH-H as NotI fragment in the NotI cutting position. Using synthetic oligonucleotides, the insert was sequenced by the method of Sanger et al. (1977, Proc Natl Acad Sci USA 74: 5463–5467). The sequence is given in Seq ID No 1.

EXAMPLE 3

Uptake Studies with $^{14}$C-labelled Methylamine into the Yeast Line 26972c::pFL61-MEP-a The yeast lines 26972c::pFL61, 26972c::pFL61-MEP-a and their starting lines S1278b (Dubois & Grenson, 1979, Mol Gen Genet 175: 67–76, MEP-1/MEP-2 ura3) were grown in liquid medium with 1.7 g yeast nitrogen base without ammonium and without amino acids (Difco), 20 g agarose, 1% glucose (w/v), 0.5 mg/l proline until the culture reached the logarithmic phase. After centrifuging of each 25 ml of the culture, the cells were washed with 10 mM phosphate pH 7 or pH 4 and taken up in 1.5 ml 10 mM phosphate buffer. Ten minutes before starting the transport measurements, it was made up to an end concentration of 10 mM glucose. 100 μml of the suspension was added to a solution of 10 mM phosphate pH 4 or 7, 100 μM unlabelled methylamine and 5 μCi $^{14}$C-labelled methylamine (0.1 mCi/1.9 μmol) (end concentrations). The uptake of the methylamine was measured after 10, 60, 120 and 180 seconds. For this, to 50 μl of starting material was taken and in a volume of 1 ml H$_2$O+3 mM unlabelled methylamine absorbed on a glass fibre filter. After washing with 10 ml H$_2$O+3 mM unlabelled methylamine the amount of $^{14}$C-labelled methylamine taken up was measured by scintillation (Table Ia and Ib). The uptake of the labelled methylamine was compared for the case of coincubation with 0.5 mM NH$_4$Cl (Table II) and 0.5 mM KCl (Table III), as well as for the case of coincubation with the uncouplers, dinitrophenol (DNP) and carbonyl cyanide m-chlorophenylhydrazone (CCCP) (Table IV). The values of a typical experiment are given in Tables I to IV:

TABLE I

Uptake of $^{14}$C-methylamine in yeast strains after incubation with 10 mM glucose at different pH values (at each time-point for the MEP-a transformants and the zero controls (plasmid pFL61 without cDNA insertion) values from two independent series of measurements are given. Measurements in cpm (counts per minute)

pH = 4
| Time point [sec] | Σ1278b | 26972c::pFL61 | | 26972c::pFL61-MEP-a | |
|---|---|---|---|---|---|
| 10 | 289.00 | 220.20 | 117.20 | 204.80 | 214.80 |
| 60 | 1151.20 | 200.60 | 138.60 | 283.80 | 345.60 |
| 120 | 19605.46 | 284.80 | 197.40 | 434.40 | 594.60 |
| 180 | 32651.43 | 317.60 | 285.60 | 479.60 | 842.20 | pH = 7
| Time point [sec] | 1278b | 26972c::pFL61 | | 26972c::pFL61-MEP-a | |
|---|---|---|---|---|---|
| 10 | 469.60 | 202.20 | ./. | 302.80 | 352.20 |
| 60 | 1022.80 | 291.80 | ./. | 1247.60 | 1292.20 |
| 120 | 6176.36 | 524.80 | ./. | 3152.50 | 3478.28 |
| 180 | 16826.67 | 797.80 | ./. | 8490.83 | 6099.39 |

TABLE II

Uptake of $^{14}$C-methylamine in yeast strains after incubation with 10 mM glucose in presence of 0.5 mM NH4Cl. Measurements in cpm. pH = 7

| Time point [sec] | 1278b | 26972c::pFL61 | 26972c::pFL61-MEP-a |
|---|---|---|---|
| 10 | 356.60 | 271.60 | 268.60 |
| 60 | 885.60 | 795.80 | 577.60 |
| 120 | 1237.80 | 1388.20 | 978.00 |
| 180 | 1597.40 | 1773.00 | 1226.60 |

TABLE III

Uptake of $^{14}$C-methylamine in yeast strains after incubation with 10 mM glucose in presence of 0.5 mM KCl, unless otherwise noted. Measurements in cpm. pH = 7

| Time point [sec] | Σ1278b | 26972c::pFL61 | 26972c::pFL61-MEP-a | 26972c::pFL61-MEP-a without KCl-competition |
|---|---|---|---|---|
| 10 | 391.20 | 127.60 | 384.00 | 205.00 |
| 60 | 2054.90 | 224.00 | 1276.60 | 467.60 |
| 120 | 8455.00 | 374.80 | 3128.44 | 1541.00 |
| 180 | 14377.14 | 567.40 | 5056.00 | 2416.39 |

TABLE IV

Uptake of $^{14}$C-methylamine in yeast strains after incubation with 10 mM glucose in presence of 0.1 mM dinitrophenol (DNP) or 10 pM carbonyl cyanide m-chlorophenylhydrazone. Measurements in cpm (counts per minute). pH = 7

| Time point [sec] | Σ1278b +DNP | Σ1278b +CCCP | 26972c::pFL61-MEP-a +DNP | 26972c::pF161-MEP-a +CCCP | 26972c::pF16-MEP-a |
|---|---|---|---|---|---|
| 10 | 167.20 | 173.20 | 378.00 | 484.60 | 373.60 |
| 60 | 386.00 | 316.80 | 1349.40 | 1407.00 | 1214.20 |
| 120 | 706.80 | 460.40 | 2794.44 | 2597.92 | 3673.45 |
| 180 | 906.00 | 608.00 | 2794.44 | 3620.36 | 6135.15 |

EXAMPLE 4

Transformation of Plants with a Construct for Over-Expression of the Coding Region of the Ammonium Transporter From the plasmid pFL61-MEP-a, that contains as insert the cDNA for the methylamine or ammonium transporter from *Arabidopsis thaliana*, the insert was isolated as NotI fragment and cloned after filling in the overhanging ends in the SmaI cutting position of pBinAR. The cDNA has the designation "B" in the plasmid map (FIG. 1). According to whether or not B is introduced in sense orientation to the 35S Promoter of pBinAR, the resulting plasmid has the designation p35S-MEP-a or p35S-a-MEP-a. The plasmid pBinAR is a derivative of pBIN19 (Bevan, 1984, Nucl Acids Res 12: 8711–8720). Between its EcoRI and KpnI cutting positions, a fragment from the genome of the cauliflower mosaic virus that carries the 35S promoter (nt 6909–7437) was introduced. The promoter fragment prepared as EcoRI/KpnI fragment from the plasmid pDH51 (Pietrzak et al., Nucl Acids Res 14: 5857–5868). In the plasmid map the promoter fragment has the designation "A". Between the SphI and the HindIII cutting position of pBinAR, the polyadenylation signal of the gene 3 of the T-DNA of the plasmid pTiACH5 (Gielen et al., EMBO J 3:835–846) is inserted.

Also a PvuII/HindIII fragment (nt 11749–11939) from the plasmid pAGV 40 (Herrera-Estrella et al., 1983, Nature 303: 209–2139) was supplied at the PvuII cutting position with a SphI linker. The polyadenylation signal has the designation "C" in the plasmid map.

After transformation of Agrobacteria with the plasmids p35S-MEP-a and p35S-a-MEP-a, these were used for infection of leaf segments of tobacco and *Arabidopsis thaliana*.

Ten independently obtained transformants for both constructs, in which the presence of the intact, non-rearranged chimeric gene was demonstrated using Southern blot analysis, were tested for changes in nitrogen content.

What is claimed is:

1. An isolated nucleic acid molecule, encoding a plant ammonium transporter, comprising a coding sequence as set forth in SEQ ID NO:1.

2. A plasmid comprising the isolated nucleic acid molecule according to claim 1.

3. The plasmid according to claim 2, further comprising a promoter sequence and a transcriptional termination sequence, the sequences operably linked to allow expression of the coding sequence, in the order: promoter sequence, coding sequence, and termination sequence.

4. The plasmid, according to claim 3, wherein the coding sequence is positioned in the sense orientation.

5. The plasmid, according to claim 3, wherein the coding sequence is positioned in the anti-sense orientation.

6. The plasmid p35S-MEP-a.

7. The plasmid p35S-a-MEP-a.

8. A yeast comprising the isolated nucleic acid molecule according to claim 1.

9. A bacterium comprising the isolated nucleic acid molecule according to claim 1.

* * * * *